(12) United States Patent
Dea

(10) Patent No.: US 6,591,142 B1
(45) Date of Patent: Jul. 8, 2003

(54) FAR INFRARED EMITTING MATERIAL FOR BODY WARMING, THERAPEUTIC PURPOSES, AND SANITATION PURPOSES

(76) Inventor: Jack Y. Dea, 4236 Feather Ave., San Diego, CA (US) 92117

( * ) Notice: Subject to any disclaimer, the term of this patent is extended or adjusted under 35 U.S.C. 154(b) by 0 days.

(21) Appl. No.: 10/057,517

(22) Filed: Jan. 28, 2002

(51) Int. Cl.[7] .................................................. A61F 2/00
(52) U.S. Cl. ........................................ 607/100; 607/96
(58) Field of Search .................... 607/96, 100, 108–111; 250/504; 5/421

(56) References Cited

U.S. PATENT DOCUMENTS

| | | | | |
|---|---|---|---|---|
| 4,680,822 A | * | 7/1987 | Fujino et al. ................... | 5/421 |
| 4,976,706 A | * | 12/1990 | Aki et al. .................... | 604/304 |
| 5,265,278 A | * | 11/1993 | Watanabe ....................... | 2/174 |
| 6,516,229 B1 | * | 2/2003 | Wey ........................... | 607/100 |

* cited by examiner

Primary Examiner—Roy D. Gibson

(57) ABSTRACT

This invention pertains to a far-infrared (FIR) material that emits strongly in a narrowly defined wavelength range. Radiation of this particular wavelength range has been found to give a warming effect to the body, give therapeutic effects and to have sanitation effects in terms of the reduction of the bacterial count. This wavelength range is also the wavelength range that the body emits which is 8 to 13 microns and peaks at 10 to 11 microns. Most materials do not strongly emit radiation in this wavelength region. The material must fit two main criteria: (1) Emits in the 8 to 14 micron range. (2) Formable so that it can be made into practical therapeutic tools. A search found a material that meets the above two requirements. It emits strongly and exclusively in the range of 9 to 12 microns and it is formable. Thus it is the ideal material for use in FIR therapeutic tools. Embodiments of several tools are described.

11 Claims, 6 Drawing Sheets

FAR INFRARED EMITTING MATERIAL FOR BODY WARMING, THERAPEUTIC PURPOSES, AND SANITATION PURPOSES

BACKGROUND OF THE INVENTION

1. Field of the Invention

The present invention relates to a far-infrared (FIR) material that emits in a narrow wavelength region and is used as the radiation emitter in therapeutic tools. This FIR material emits strongly and exclusively in the 9 to 12 micron wavelength range. It is used passively as a heating pad when the heat from the body stimulates the FIR emission. It is used as an active emitter when it is the hot element of a therapeutic device such as a heat massager.

2. Technical Background

In the last two decades Japanese scientists and physicians have discovered that far infrared (FIR) waves have therapeutic and sanitary effects. Many Japanese patents have been filed in Japan covering FIR technology. Some patents have been applied for in the U.S. Generally, they describe a particular ceramic that emits FIR waves or a process to coat FIR ceramics onto heating elements.

Near infrared waves are waves with wavelengths between 0.8 and 3 microns. FIR waves are long wavelength radiation with a wavelength longer than 3 microns. Usual FIR emitting materials are the ceramic oxides. They include magnesium oxide, aluminuma silicates, quartz (silicon dioxide), iron oxide, aluminum oxide, zirconium oxide, and titanium dioxide. While these materials are good FIR emitters, the radiation emitted is generally broad, covering typically 3 to 15 microns.

Major uses for far-infrared rays are in therapeutics and in sanitation. Patents found that are related to therapeutics are listed in references 1, 2 and 3. The patent related to sanitation is reference 4. Reference 1 describes fibers that are made from far-infrared emitting materials and are made into in clothing. Reference 2 describes a powder and fibers made from the powder that have high far-infrared emissivity. The powders and fibers are made into therapeutic clothing and sanitary wraps. Reference 3 describes a far-infrared lamp that emits strongly in the 8 to 9 micron region. The radiation in this region is claimed to be highly therapeutic. Reference 4 describes an apparatus that sterilizes articles placed inside through bombardment with far-infrared radiation.

The human body emits strongly in the 8 to 13 micron range, peaking at 10 to 11 microns. DNA has been found to have strong absorption at 11 microns. Therapeutic effects and sanitation effects are also strongest in this region. Therefore, the most efficient FIR material for use in therapeutics and sanitation would emit strongly in the 8 to 13 micron region and little elsewhere. However, prior art does not cover efficiently this wavelength region. References 1 and 2 describe inventions that emit broad band FIR radiation. Reference 3 describes a narrow band FIR device (8 to 9 microns) of rather complicated construction. For these reasons a search was conducted to find a more suitable FIR material. The material must meet two main criteria: (1) Strongly emits in the 8 to 13 micron region and little elsewhere. (2) Formable so as to be easily formed into therapeutic tools.

SUMMARY OF THE INVENTION

A search was conducted to find a material that meets the requirements of emission characteristics (8 to 13 microns) and formability. The search was conducted both experimentally and through the literature. Experimentally, different materials were examined using a FTIR (Fourier Transform Infra-Red) spectrometer. Literature wise, published far-infrared spectra were collected from various library sources. This search has found a material that exclusively and strongly emits (and hence also absorbs) radiation in the 9 to 12 micron band. This material is almost transparent to infrared waves below 9 microns and above 12 microns in wavelength. The material is polyvinylfluoride (PVF). FIG. 1 shows a schematic of its emission characteristics. The oxide materials mentioned above generally do not have such specific emission characteristics.

This document discloses the application of a FIR material for two therapeutic tools. The first tool is that of a passive heating pad. The FIR material, in sheet form, is first coated with silver, through a process such as vacuum sputtering. The silver provides two functions: First as a surface of low emissivity so that the emissions from the FIR material dominates. Second, the silver reflects back heat to prevent heat loses. The silvered side is then laminated to a rubber sheet substrate to provide support. The FIR sheet is about 1.5 mil thick and the rubber substrate is about 10 mil thick. These thicknesses can be varied. This heating pad is shown in FIG. 2. A large pad is used as a mattress pad. A medium pad is used as a local body pad. A small pad is used as an insole for shoes.

The prototype pad was tried as a mattress pad and as a shoe insole. The prototype mattress pad gave an immediate comfortable warm feeling. It is a pleasant warmth and not a hot feeling. The amount of sleep was reduced immediately. Overall, an improvement in well-being was noted.

To explain the function of comfort due to a feeling of increased warmth, it is noted that body temperature varies very little from 98.6 degrees F. or about 38 degrees C. At this temperature the body IR emission peaks at about 10 to 11 microns. Hence IR rays of this wavelength are comfortable to the body. An increase in the 10 to 11 micron radiation, as provided by the FIR sheet, without radiation outside the 9 to 12 micron window, provides a "cool" warmth. By "cool" we mean a feeling of warmth and comfort without a great deal of heating of the body as would be the situation with most emitting surfaces. The heat from the FIR material is selectively absorbed in the DNA and in breaking up water clusters. With most other emitting surfaces the broad band radiation mostly goes to heating up the body. The body is mostly water and broad band IR radiation will heat up water. On the other hand, the DNA absorption and breaking up of water clusters are useful functions that don't contribute directly to heating up the body. All these reasons contribute to the comfortable "cool" heat provided by FIR material.

One explanation of the feeling of well-being lies with cellular absorption and elimination. The water that we drink comes in clusters of water molecules. The clusters can range from one molecule to dozens of molecules. The clusters are broken up most efficiently in the far infrared ranges. Water cluster size is important in cellular activity. The smaller clusters, working in groups, are able to wrap around ions and transport them. The larger clusters have more difficulty in trapping ions. An additional reason for difficult transport is the size which makes intermembrane transport easier for smaller clusters and smaller cluster/ion units and difficult for large clusters. Thus, intermembrane transport, which is important in cellular absorption and elimination, is enhanced with smaller water clusters.

A second application is the use of the FIR material as the hot emitting element in a heat/cold massager. It is also the cold absorbing element in the heat/cold massager. This heat/cold massager consists of a Peltier junction thermoelectric heat pump. The heat pump consists of two aluminum plates separated by a series of Peltier junctions. With power on, one aluminum plate will be hot and the other plate will be cold. A heat/cold massager unit is made by laminating the FIR material, in sheet form, to both aluminum plates. FIG. 3 shows a schematic of this device. Thus, the hot side is used to provide FIR heat to a part of the body. The other side is to provide "cold", that is, it acts as a heat sink by absorbing 9 to 12 micron radiation. The hot and cold plates do not touch the body but perform their operation at a distance through FIR radiation. One method to prevent touching is through the use of FIR transparent covers over the plates.

The prototype unit provides a heating effect similar to the heating pad but at a higher level to a smaller area. The cold operation also gave a comfortable feeling. Headaches and inflammations, such as burning eyes, are helped with the cold operation.

Another important FIR function is in sanitation. Japanese scientists have shown that bacteria growth is slowed and stopped by FIR radiation. How this mechanism works is uncertain at present (reference 4). The FIR pad and the FIR massager as described in this document are also presumed to work against bacteria growth.

We have disclosed a FIR material and its application in two devices. The first device is a heating pad. The second device is a heat/cold massager. Both the pad and massager give a feeling of warmth and comfort and improves cellular health. Thus, the overall well-being and health of the user is improved with this invention. An additional benefit is the sanitation effect of reduced bacterial activity.

DESCRIPTION OF THE PREFERRED EMBODIMENT

Figure 1:
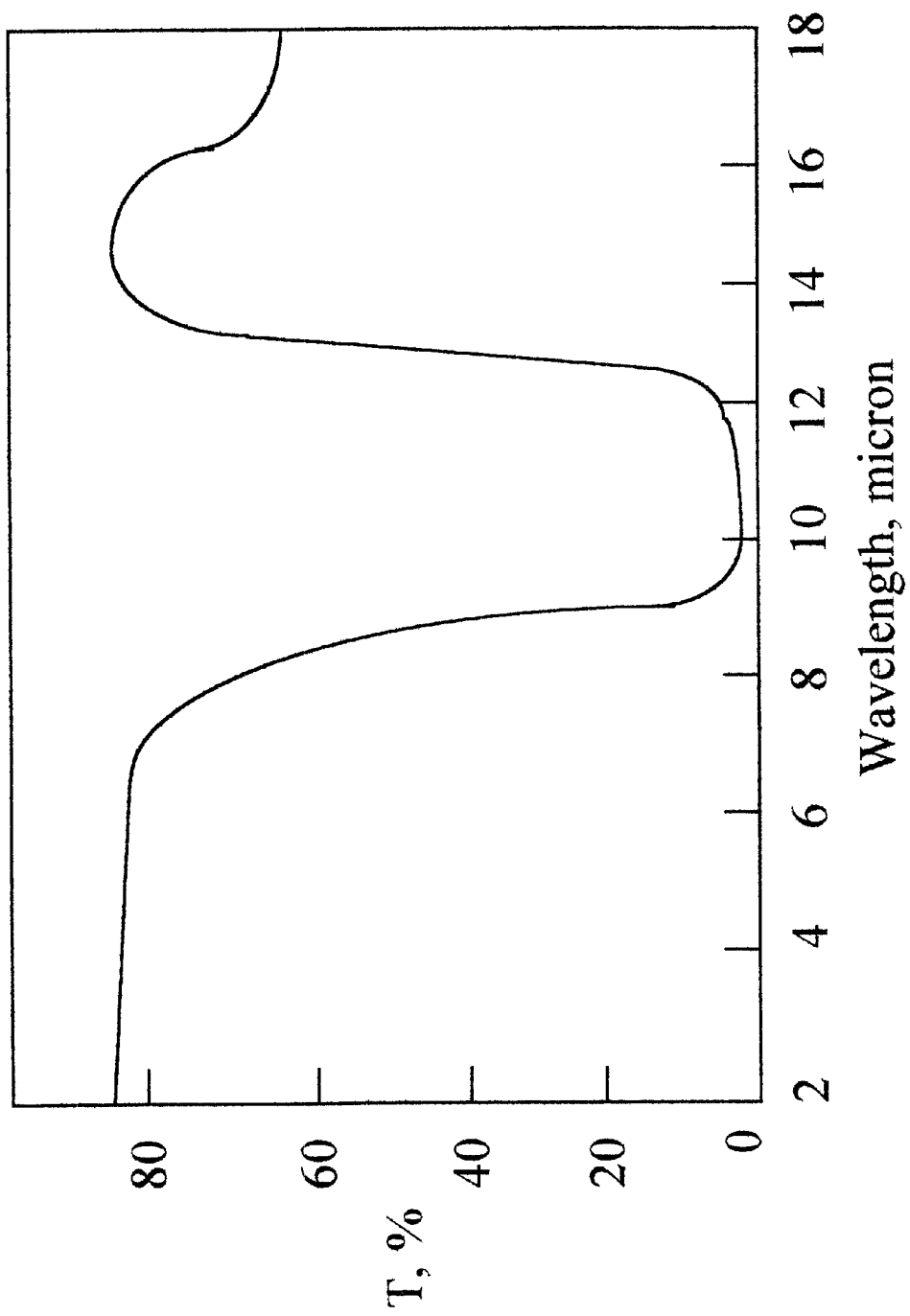
FIG. 1 is a graph of a transmission spectrum of a FIR sheet of PVF material.

The invention will be described by referring to FIGS. 1–6 of the drawings. FIG. 1 illustrates a graph of the transmission spectrum of a FIR sheet.

Figure 2:
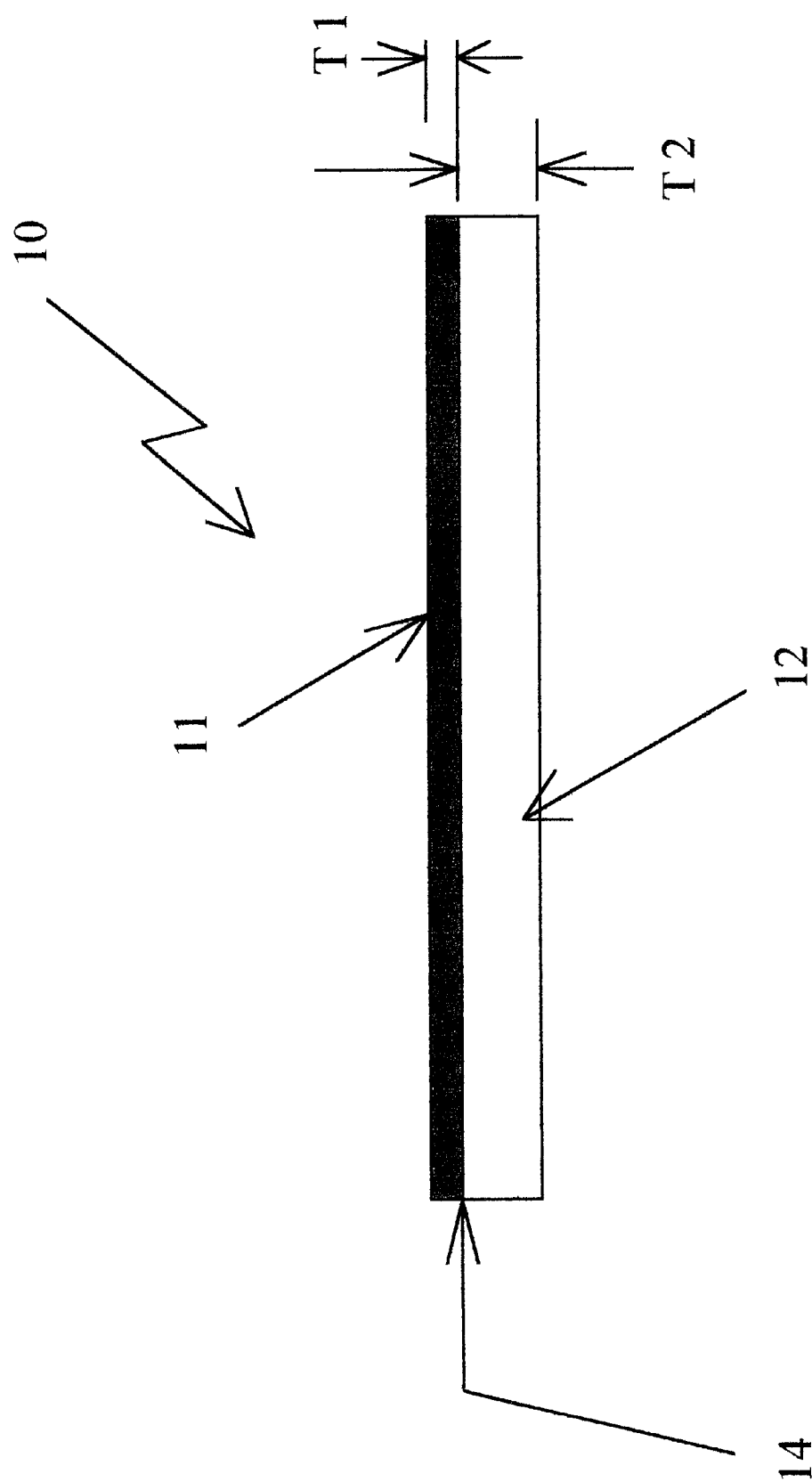
FIG. 2 is a schematic cross-sectional view of a passive FIR heating pad.
Figure 4:
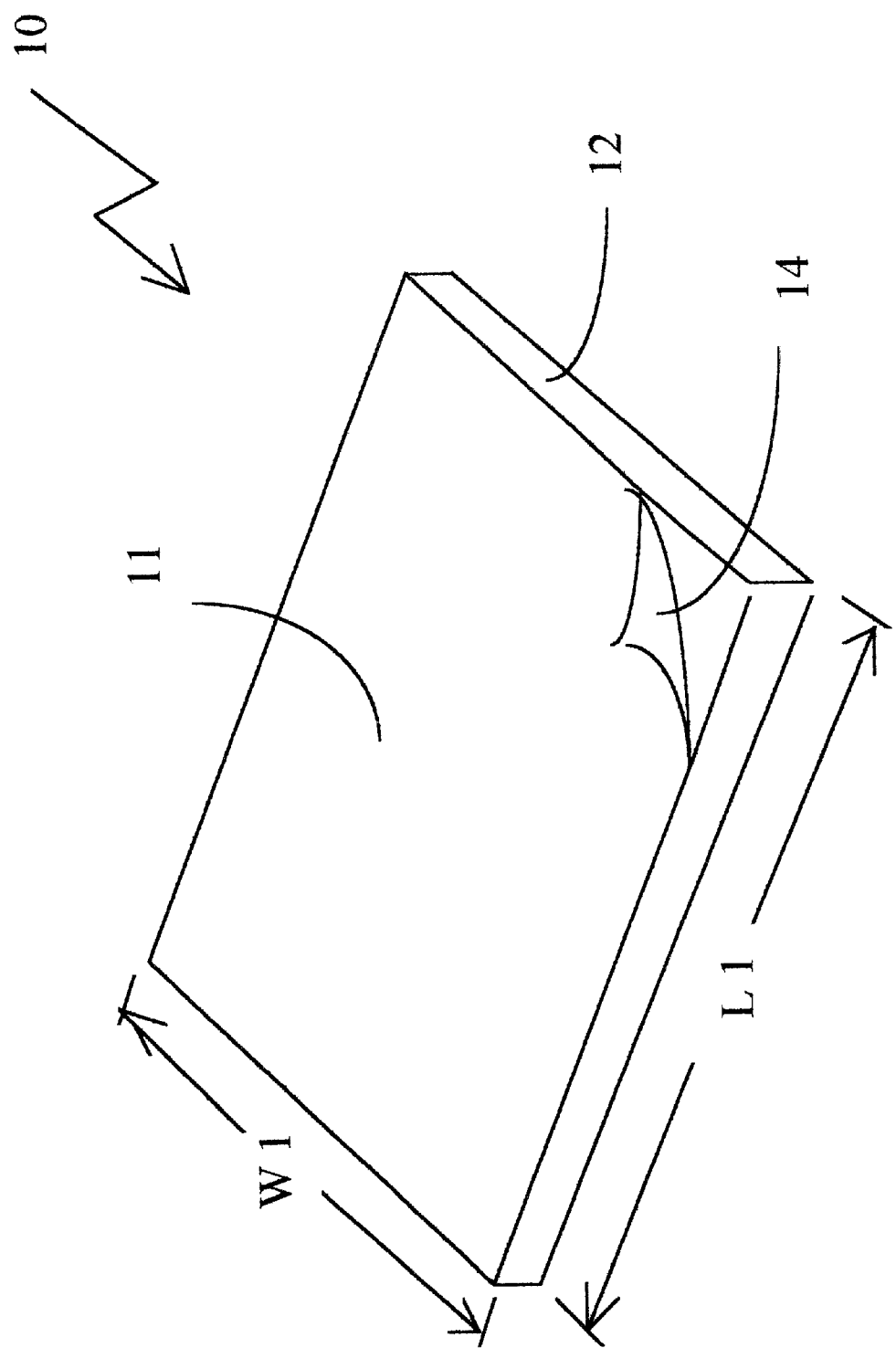
FIG. 4 is a front perspective view of a passive FIR heating pad.
Figure 5:
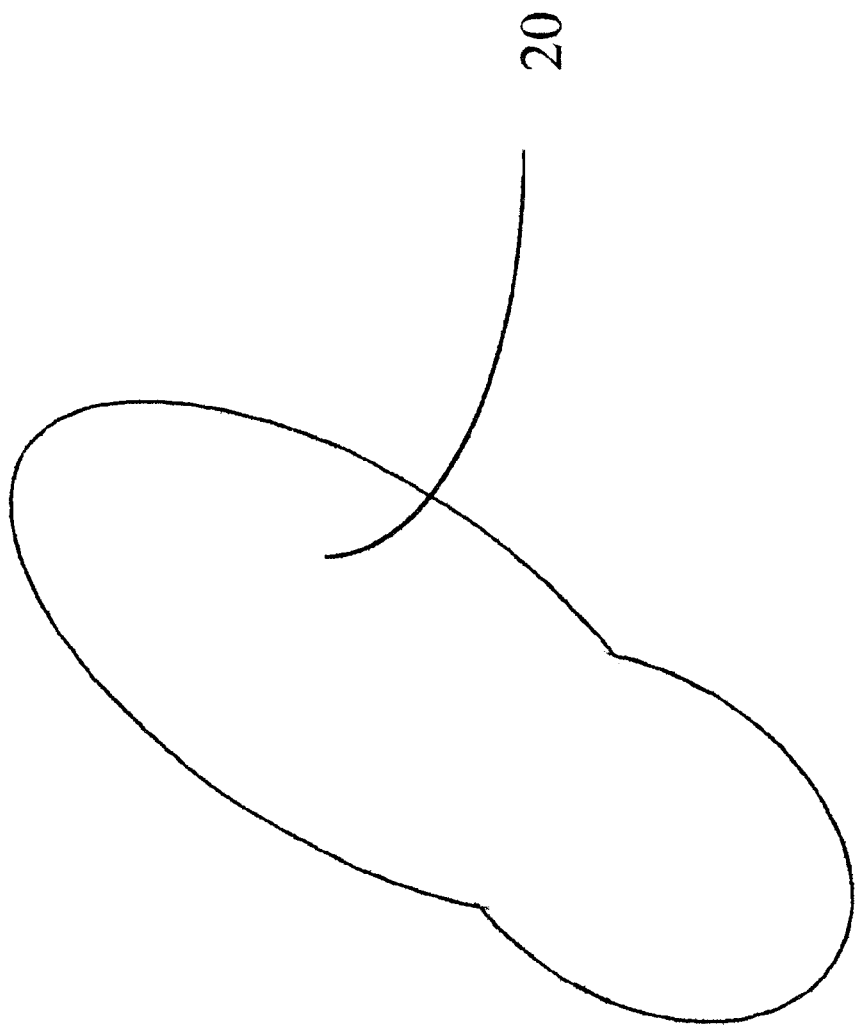
FIG. 5 is a top plan view of a passive FIR heating pad in the shape of an insole for a shoe.

FIGS. 2 and 4 illustrate a FIR heating pad 10. It has a top sheet 11 of polyvinylfluoride (PVF) with a silver coating 14 on its bottom surface. A rubber substrate 12 is laminated to the bottom surface of silver coating 14. Heating pad 10 has a length L1 in the range of 1–96 inches and a width W1 in the range of 1–96 inches. In its larger size it is used as a mattress pad. In smaller sizes it is used as a local body pad. FIG. 5 shows the passive FIR heating pad in the shape of an insole 20 for a shoe. Sheet 11 has a thickness T1 in the range of 0.5–5.0 mils. Rubber substrate 12 has a thickness T2 in the range of 3–20 mils.

Figure 3:
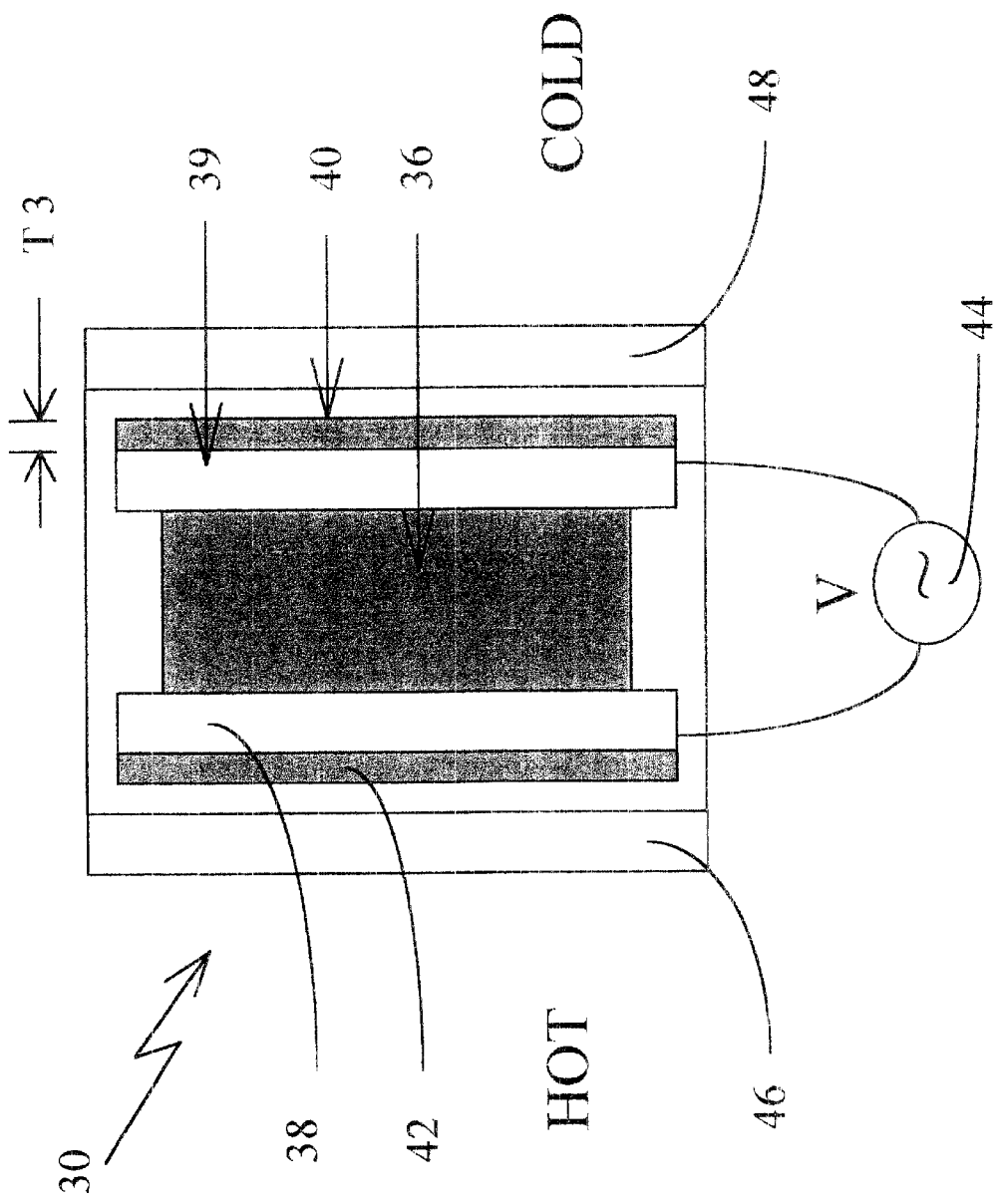
FIG. 3 is a schematic cross-sectional view of a Peltier junction heat/cold massager with FIR surface.
Figure 6:
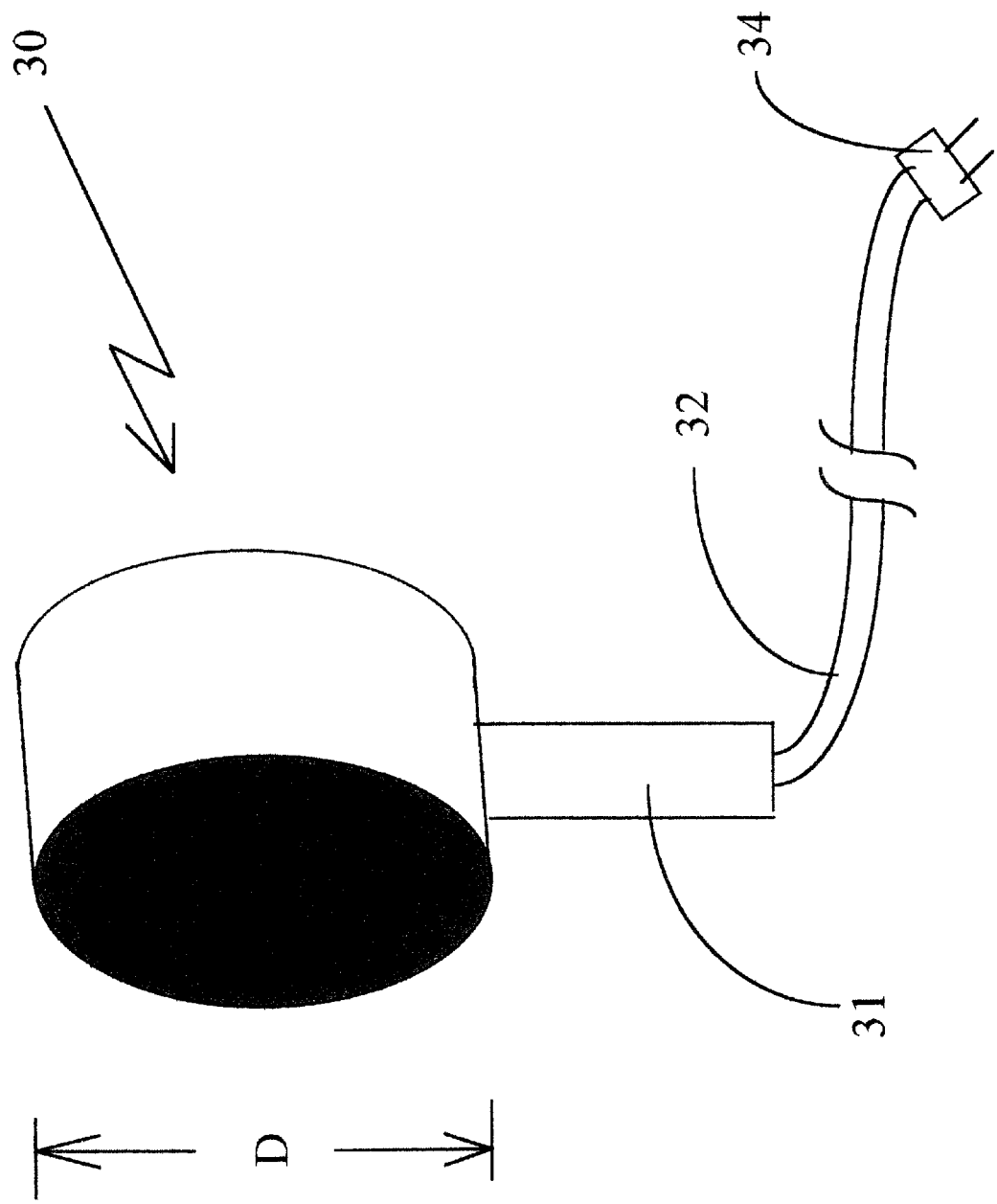
FIG. 6 is a front perspective view of a Peltier junction heat/cold massager with FIR surface.

A Peltier junction heat/cold massager 30 is illustrated in FIGS. 3 and 6. It has a diameter D in the range of 2–6 inches.

It has an electrical cord 32 having a male plug 34 for connecting it to an A.C. wall socket. It has a handle 31 for ease of handling.

The schematic cross sectional view of the heat/cold massager 30 shows that it has a semi-conductor layer 36 having a top aluminum plate 38 and a bottom aluminum plate 39 connected to its respective top and bottom and bottom surfaces. A bottom PVF sheet 40 is attached to the bottom surface of aluminum plate 39. A top PVF sheet 42 is attached to the top surface of aluminum plate 38. An alternating current source 44 is connected to the respective top and bottom aluminum plates 39 and 38. As an option, a top cover sheet 46 and a bottom cover sheet 48 can be laminated to the respective top and bottom sheets 40 and 42. Cover sheets 46 and 48 would be made of an IR transparent polyethylene plastic material. Top and bottom FIR (PVF) sheets 40 and 42 have a thickness T3 in the range of 0.5—5.0 mils.

REFERENCES:
1. U.S. Pat. No. 4,999,243. "Far Infrared Radiant Composite Fiber". Nobushige Maeda, Mar. 12, 1991.
2. U.S. Pat. No. 5,258,228. "Infrared Slight Energy Radiation Powder and Synthetic Fiber Containing Said Powder Mixed Therein and Fiber Articles Comprising Said Fiber". Toshio Komuro, Nov. 2, 1993.
3. U.S. Pat. No. 4,816,689. "Device serving to Generate Infrared Radiation Effective on Cutaneous and Deep-seated Tissue of the Body". Umberto Cavicchi, Mar. 28, 1989.
4. U.S. Pat. No. 5,039,865. "Sanitation Apparatus". Masashi Koji, Aug. 13, 1991.

What is claimed is:

1. A thermal pad comprising:

a sheet of flexible far-infrared(FIR) material having a left edge, a right edge, a front edge, a rear edge, a top surface and a bottom surface; said sheet having a length L1, a width W1 and a thickness T1; a coating of silver is formed on said bottom surface of said sheet of FIR material;

a sheet of flexible rubber substrate having a top surface, a bottom surface, a left edge, a right edge, a front edge and a rear edge; said sheet having a length L1, a width W1 and a thickness T2;

adhesive means securing said silver coated bottom surface of said sheet of FIR material to the top surface of said sheet of rubber substrate; and said FIR material exhibiting the properties of emitting radiation substantially only in the 9–12 micron band and only absorbing radiation substantially only in the 9–12 micron band.

2. A thermal pad as recited in claim 1 wherein L1 is in the range of 1–96 inches and W1 is in the range of 1–96 inches.

3. A thermal pad as recited in claim 2 wherein said pad is formed in the shape of an insole for a shoe.

4. A thermal pad as recited in claim 2 wherein T1 is in the range of 0.5–5 mils thick.

5. A thermal pad as recited in claim 2 wherein T2 is in the range of 3–20 mils thick.

6. A thermal pad as recited in claim 1 wherein said FIR material is a sheet of polyvinylfluoride (PVF).

7. A heat/cold massager comprising:

a top sheet and a bottom sheet of flexible far-infrared(FIR) material and each sheet has a circular edge, a top surface and a bottom surface; each sheet having a diameter D and a thickness T3;

a top aluminum plate and a bottom aluminum plate and each have a top surface and a bottom surface;

said top sheet of FIR material being laminated on said top surface of said top aluminum plate; said bottom sheet of FIR material being laminated on said bottom surface of said bottom aluminum plate;

a semiconductor layer sandwiched between said bottom surface of said top aluminum plate and the top surface of said bottom aluminum plate;

means for connecting an electrical circuit between said top and bottom aluminum plates; and said FIR material exhibiting the properties of emitting radiation substantially only in the 9 to 12 micron band and absorbing radiation substantially only in the 9 to 12 micron band.

8. A heat/cold massager as recited in claim 7 wherein D is in the range of 2–6 inches.

9. A heat/cold massager as recited in claim 7 wherein T3 is in the range of 0.5–5 mils thick.

10. A heat/cold massager as recited in claim 7 wherein said FIR material is a sheet of polyvinylfluoride (PVF).

11. A heat/cold massager as recited in claim 7 further comprising a sheet of infrared transparent polyethylene plastic covering said top surface of said top sheet of FIR material and a sheet of infrared transparent polyethylene plastic covering said bottom surface of said bottom sheet of FIR material.

* * * * *